United States Patent [19]

Kohmaier

[11] 4,237,717

[45] Dec. 9, 1980

[54] METHOD OF MANUFACTURING ROLLERS

[76] Inventor: Franz Kohmaier, Trazerberggasse 78, 1130 Wien, Austria

[21] Appl. No.: 42,061

[22] Filed: May 24, 1979

[30] Foreign Application Priority Data

May 23, 1978 [AT] Austria ................................ 3723/78

[51] Int. Cl.³ ............................................. B21B 31/06
[52] U.S. Cl. ...................................... 72/364; 72/368; 148/11.5 R; 148/155; 59/8
[58] Field of Search .................................. 51/314, 316; 148/11.5 R, 130, 155; 72/53, 342, 364, 368; 59/8, 29, 30, 35 R, 35 CP, 5

[56] References Cited

U.S. PATENT DOCUMENTS

| 1,387,199 | 8/1921 | Small | 72/368 |
| 1,925,055 | 8/1933 | Mize | 59/5 |
| 3,706,199 | 12/1972 | Zimmer | 59/8 |

Primary Examiner—Lowell A. Larson
Attorney, Agent, or Firm—Michael J. Striker

[57] ABSTRACT

Rollers are manufactured by winding a metallic band piece so that ends of the band piece butt against and are flush with one another, and heating and hardening the wound band piece. A striking load is applied during the heating step so that a gap which tends to form after winding between the ends of the band piece is closed. The application of the striking load may be performed by raising and dropping the wound band pieces. The latter may be done in a rotary furnace, or in a retort furnace with an inclined conveyor. Advantageously, the heating and hardening are performed after calibrating of the wound band pieces.

10 Claims, 4 Drawing Figures

METHOD OF MANUFACTURING ROLLERS

BACKGROUND OF THE INVENTION

The present invention relates to a method of manufacturing rollers, particularly rollers for roller chains. More particularly, it relates to such a method which includes winding of a metallic band piece on a mandrel so that the ends of the band piece abut against one another and are flush with one another, and heating and hardening the wound band piece advantageously after calibrating of the same.

The following three methods are generally utilized for manufacturing of rollers: cross-cutting of seamless pulled or welded tubes, deep drawing, and winding in accordance with the above-listed manufacturing steps. The winding method is the most favorable in the sense of material economy and labor economy since the wastes in the cross-cutting method are equal to approximately 20% and in the deep-drawing method are equal to approximately 40%. However, the known winding method has the following disadvantage: In dependence upon the dimensions of the roller, a gap is formed, after winding, between the juxtaposed ends of the metallic band piece, which gap is equal to approximately 0.1 mm. During the thermal treatment this gap becomes even larger. In order to reduce or close this gap, the hardened rollers are subjected to an additional treatment, particularly to ball blasting. As a result of the ball blasting, the outer layer of the wound band pieces elongates and the rollers are partially closed. However, the ball blasted rollers have a very high surface roughness whereby they must be polished after blasting.

SUMMARY OF THE INVENTION

Accordingly, it is an object of the present invention to provide a method of manufacturing rollers, which avoids the disadvantages of the prior art.

More particularly, it is an object of the present invention to provide a method of manufacturing rollers, in accordance with which a gap formed between juxtaposed ends of a metallic band can be reliably closed in a simple and inexpensive manner.

In keeping with these objects and with others which will become apparent hereinafter, one feature of the present invention resides, briefly stated, in a method in which a wound metallic band piece is subjected to a striking load during its heating whereby a gap formed between juxtaposed ends of the metallic band piece is closed.

When the rollers are manufactured in accordance with the above-described method, the gap formed between the ends of the wound metallic band piece is closed in an inexpensive and simple manner. The method does not utilize ball blasting which increases roughness of the roller surface. The closed gap does not open during subsequent application of loads. Since the known method of manufacturing the rollers always includes heating of the wound band pieces so as to harden the same, no additional expenses are required for performing the inventive method.

In accordance with another advantageous feature of the present invention, the application of a striking load is performed by raising and dropping the rollers during their heating. This makes the inventive method even more simple and inexpensive. The raising and dropping of the rollers is conducted continuously and advantageously in such a manner that the raising step is performed forcedly, whereas the dropping step is performed under the action of forces of gravity. Thereby, reliable closing of the gap between the ends of the metallic band pieces is attained.

In accordance with still another feature of the present invention, the raising and dropping step is performed in a rotary furnace so that when the furnace rotates, the wound bands are raised and dropped, while being simultaneously subjected to the action of heat in the furnace. Advantageously, the furnace continuously rotates with a speed equal to substantially 0.5 revolution per second.

A further feature of the present invention is that the raising and dropping step may be performed by an inclined conveyor located in a retort furnace. In such a case the wound band pieces or rollers are raised to the highest point of the conveyor wherefrom they drop under the action of their weight. At the same time, the wound band pieces are subjected to heat existing in the interior of the furnace.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

A roller, particularly a roller for roller chains, is manufactured from a metallic band piece which is wound so that its ends abut against and are flush with one another. The winding may be performed on a mandrel. After this, the wound band piece is advantageously calibrated. The thus-worked band piece is then heated and hardened.

Figure 1:
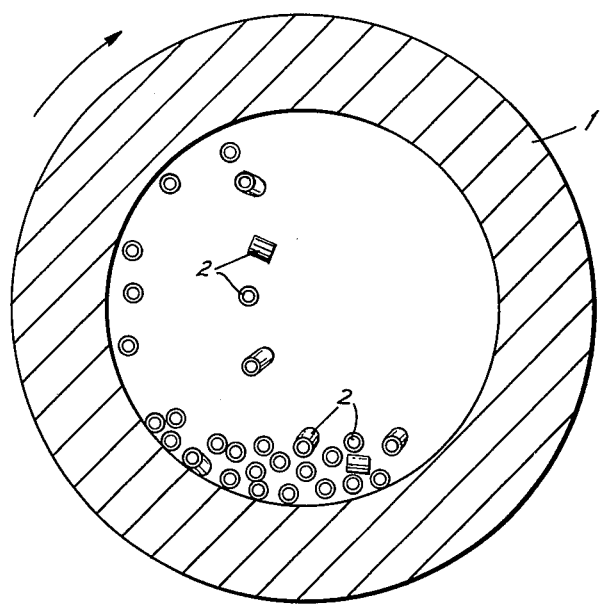
FIG. 1 is a view showing a rotary furnace in which rollers are manufactured in accordance with the inventive method.

In accordance with the present invention, a striking load is applied to the wound band piece during the heating step. This may be performed as shown particularly in FIG. 1. FIG. 1 schematically shows a rotatable part or a drum 1 of a rotary furnace. Any suitable rotary furnace may be utilized, for example the furnace Aichelinofen Type TRG-2 manufactured by "Aichelin Industrieofenbau", West Germany. A plurality of wound band pieces 2 are loaded into the rotatable drum 1 of the rotary furnace and the drum is driven in rotation. Being accommodated in the drum 1, the wound band pieces 2 are subjected to heat treatment. At the same time, during the rotation of the drum 1 the wound band pieces are raised upwardly along an inner surface of the drum 1 and then drop downwardly under the action of force of gravity. Advantageously, the drum 1 rotates with a speed equal to substantially 0.5 revolutions per second. However, it can rotate with another speed, in dependence upon the dimensions of the drum and the rollers to be manufactured.

A cold rolled strip of heat-treatable steel SAE 1045 may be utilized as an initial material for manufacturing the rollers. This material does not have pure martensite structure after hardening, and as a result of its non-uniform structure additional strain is likely obtained which is favorable for producing the rollers by hardening. Also cold rolled strip of heat-treatable steel SAE 1015 may be utilized for manufacturing the rollers in accordance with the present invention. The initial cold rolled strip is gradually fed, notched, and cut through so as to form the above-mentioned band pieces which are wound on a mandrel. After this, the wound band pieces are calibrated and pulled through a drawing die. It is understood that other materials may also be utilized for manufacturing the rollers. The wound band pieces 2 are heated in the drum 1 of the rotary furnace to temperatures equal to between 880° and 940°. For the band pieces of SAE 1045 these temperatures are advantageously equal to 880°-930°, whereas for the band pieces of SAE 1015 they are advantageously equal to 910°-940°. As indicated above, the drum 1 generally rotates with a speed of 0.5 revolutions per second. When the above-mentioned hardening temperatures are reached, the speed of rotation of the drum 1 is changed to one revolution per second. At this speed of rotation, centrigufal force and friction force compensate each other, and the wound band pieces or rollers 2 are transported by the rotating drum 1 upwardly, wherefrom they drop downwardly under the action of their own weight. This process is performed during approximately half an hour, and thereafter the rollers are dipped into a suitable oil bath.

Figure 3:
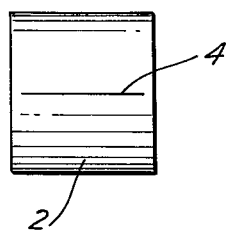
FIGS. 3 and 4 are axial and side views, respectively, of the rollers manufactured in accordance with the inventive method.
Figure 4:
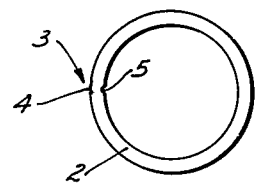

FIGS. 3 and 4 show a roller manufactured in accordance with the above-described method. The roller shown in these Figures has an outer diameter equal to 15.8 mm and an inner diameter equal to 11.4 mm, so that the wall thickness of the roller is equal to 2.2 mm. In the region 3 of juxtaposed ends outside of the band piece forming the roller, the materials of the ends are fully connected with one another. A shallow notch 4 extends between edges of the roller and disappear near the edges. In the region of the juxtaposed ends inside of the band piece forming the roller, a narrowed slot 5 extends approximately to the center of the roller. It has been shown from practice, that the thus-manufactured rollers are not opened even in condition of the highest loads.

Figure 2:
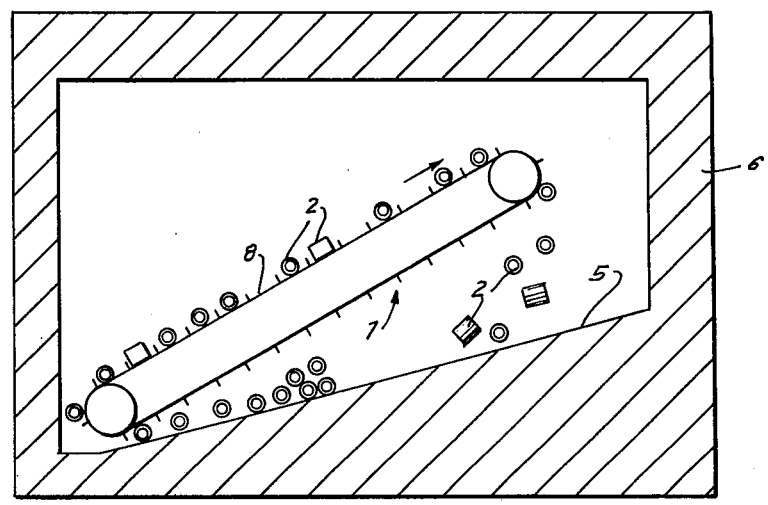
FIG. 2 is a view showing a conveyor accommodated in a retort furnace, for manufacturing the rollers in accordance with the present invention.

FIG. 2 shows another arrangement for manufacturing the rollers in accordance with the inventive method. The arrangement includes a retort furnace 6 in which an inclined conveyor 7 is provided. The wound band pieces 2 are subjected to heat treatment in the furnace 6. At the same time they are transported upwardly by an advancing run 8 of the conveyor 7 formed, for example, as a plate conveyor. When the wound band pieces 2 reach the highest point of the conveyor 7, they drop downwardly and slide back over an inclined bottom 9 of the furnace to the initial part of the conveyor 7. Thereby, a striking load is continuously applied to the wound band piece 2 during their heating in the furnace.

It will be understood that each of the elements described above, or two or more together, may also find a useful application in other types of constructions differing from the types described above.

While the invention has been illustrated and described as embodied in a method of manufacturing rollers, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly consitute essential characteristics of the generic or specific aspects of this invention.

I claim:

1. A method of manufacturing rollers, particularly for roller chains, comprising the steps of providing a metallic band having two spared ends; winding the metallic band so that the ends of the metallic band abut against and are flush with one another; heating and hardening the wound metallic band after said winding step; and applying a striking load to the wound metallic band during said heating step so as to close a gap which forms between the ends of the metallic band.

2. A method as defined in claim 1, wherein said winding step includes winding of the metallic band about a mandrel.

3. A method as defined in claim 1; and further comprising the step of calibrating the wound metallic band before said heating step.

4. A method as defined in claim 1, wherein said applying step includes raising and dropping the wound metallic band during said heating step.

5. A method as defined in claim 4, wherein said raising and dropping is performed continuously.

6. A method as defined in claim 4, wherein said raising step is performed forcedly, wherein said dropping step is performed under the action of force of gravity of the wound metallic band.

7. A method as defined in claim 4, wherein said raising and dropping step includes accommodating the wound metallic band in a rotary furnace and rotating the latter so that the wound metallic band is continuously raised and dropped during the rotation of the rotary furnace.

8. A method as defined in claim 7, wherein the rotary furnace rotates with a speed which is equal to substantially 0.5 revolution per second.

9. A method as defined in claim 4, wherein said raising and dropping step includes transporting the wound metallic band by an inclined conveyor so that the metallic band is advanced upwardly to a highest point of the conveyor and after this is dropped downwardly from the latter.

10. A method as defined in claim 10, wherein said conveyor is accommodated in a furnace so as to perform said raising and dropping step by the conveyor during heating of the wound metallic band in the furnace.

* * * * *